United States Patent [19]

Maurer

[11] 4,157,948

[45] Jun. 12, 1979

[54] OXYGEN SENSOR TO DETERMINE THE OXYGEN CONTENT IN GASES

[75] Inventor: Helmut Maurer, Schwieberdingen, Fed. Rep. of Germany

[73] Assignee: Robert Bosch GmbH, Stuttgart, Fed. Rep. of Germany

[21] Appl. No.: 883,452

[22] Filed: Mar. 6, 1978

[30] Foreign Application Priority Data

Mar. 9, 1977 [DE] Fed. Rep. of Germany ....... 2710218

[51] Int. Cl.² ............................................ G01N 27/46
[52] U.S. Cl. .................................. 204/195 S; 204/1 T
[58] Field of Search ............................ 204/1 S, 195 S; 23/254 C

[56] References Cited

U.S. PATENT DOCUMENTS

| | | | |
|---|---|---|---|
| 3,546,086 | 12/1970 | Satles | 204/195 S |
| 3,676,820 | 7/1972 | Taguchi | 23/254 E |
| 3,909,385 | 9/1975 | Spielberg et al. | 204/195 S |
| 3,597,345 | 8/1971 | Hickam et al. | 204/195 S |
| 4,005,001 | 1/1977 | Pebler | 204/195 S |
| 4,013,943 | 3/1977 | Chou et al. | 23/245 E |
| 4,049,524 | 9/1977 | Togawa et al. | 204/195 S |

FOREIGN PATENT DOCUMENTS 1954663 5/1970 Fed. Rep. of Germany.
2547683 5/1976 Fed. Rep. of Germany.

*Primary Examiner*—T. Tung
*Attorney, Agent, or Firm*—Flynn & Frishauf

[57] ABSTRACT

To provide rapid, external heating of a solid electrolyte body exposed to gases, the solid electrolyte is applied, for example by plasma spraying, to a disk-like metallic carrier plate which has an insulated coating thereover, in which the carrier plate is formed with openings throughout its circumference leaving connecting strips between the openings. Heating current conductors are connected at locations opposite the openings so that the connecting strips will form resistance paths heating the electrolyte body on the plate. A catalytically inactive electrode is applied to the electrolyte at one side of the plate, and a catalytically active coating is applied to the electrolyte at the other side of the plate. For use in sensing oxygen content of automotive vehicles, the plate is preferably held by spacers on a socket, and the spacers form terminals for both one of the heating electrodes and the electrolyte body electrodes, the other terminals being suitably connected to the plate, and to the electrolyte body, respectively.

14 Claims, 3 Drawing Figures

OXYGEN SENSOR TO DETERMINE THE OXYGEN CONTENT IN GASES

The present invention relates to a sensing element to determine the oxygen content in gases, and more particularly to an oxygen sensor to determine the oxygen content in the exhaust gases of internal combustion engines.

BACKGROUND AND PRIOR ART

Oxygen sensors using a solid electrolyte body on which a catalytically active electrode and a catalytically inactive electrode are applied have previously been proposed.—see German Patent Disclosure Document DE-OS No. 2 547 683, based on U.S. application Ser. No. 524,674, Riddel. It has also been suggested that the solid electrolyte should be capable of being heated, typically being electrically heated. (see e.g. U.S. Pat. No. 3,597,345).

External heating of the solid electrolyte body of such a sensor has the advantage that it can be rendered active quickly and that its heating will not be dependent on the temperature of the gases, the oxygen of which it has to sense. Thus, the oxygen sensing capability can be obtained even upon cold starting of an internal combustion engine with which the sensor is used. An output signal can be obtained quickly. Heating the sensor has the additional advantage, specifically when used with automotive-type internal combustion engines, that lead is not precipitated on the sensor if the fuel used in the engine contains lead. Such lead has the tendency to precipitate on cold sensing elements. Heated sensors are particularly applicable and may be necessary where the exhaust gases must pass a substantial distance from the combustion chamber of the engine until they meet the sensor, for example in installations in which the exhaust gases from various cylinders of a multi-cylinder internal combustion engine can be combined only a substantial distance away from the cylinders. Heated sensors are especially useful and, indeed, may be necessary in opposed piston engines, in V-type engines, or the like, having separate exhaust manifolds for different cylinders or cylinder banks from which the exhaust gases are combined in a single exhaust duct.

Sensors which can be heated usually were so constructed that a separate heating winding was used to heat a solid electrolyte or a carrier therefor. In many instances the amount of heat which can be applied to the solid electrolyte or the carrier was insufficient so that the desired aim of rapid sensing capability of the sensor, and avoidance of precipitation of lead was achieved only partially and insufficiently. Yet, the additional heating winding caused additional costs and space for the sensor.

THE INVENTION

It is an object to provide a sensor structure in which the additional structural and electrical elements necessary for heating the sensor are reduced to a minimum, which has a short heating period so that the operating temperature of the solid electrolyte is reached rapidly, and which does not require additional space for installation of the sensor in the exhaust system of an engine, typically an internal combustion engine.

A carrier in form of a metallic disk-like plate, typically a circular plate, is provided which has two heater current connections. The carrier plate is formed with openings leaving connecting strips between the openings which provide heating resistance paths between the heater connections. The plate, including the edges and internal rims of the openings is entirely coated with an insulating material. A solid electrolyte covering is applied to the plate including the insulated-coated internal rims of the openings. A catalytically inactive electrode is applied to the solid electrolyte body at one side of the plate, and a catalytically inactive electrode to the solid electrolyte body at the other side of the plate.

In a preferred form, the plate is a circular disk, with one heater connection applied to the center and return heater connections provided by support struts connected to the edges of the plate.

The sensor provides the advantage that the narrow connecting strips between the openings provide high resistance paths ensuring rapid heating of the plate; these connecting strips form direct heater elements heating the carrier body which is necessary in any event for the solid electrolyte. This permits rapid heating of the solid electrolyte while the additional structural requirements to heat the electrolyte are reduced to a minimum.

Drawings, illustrating a preferred example:

Figure 1:
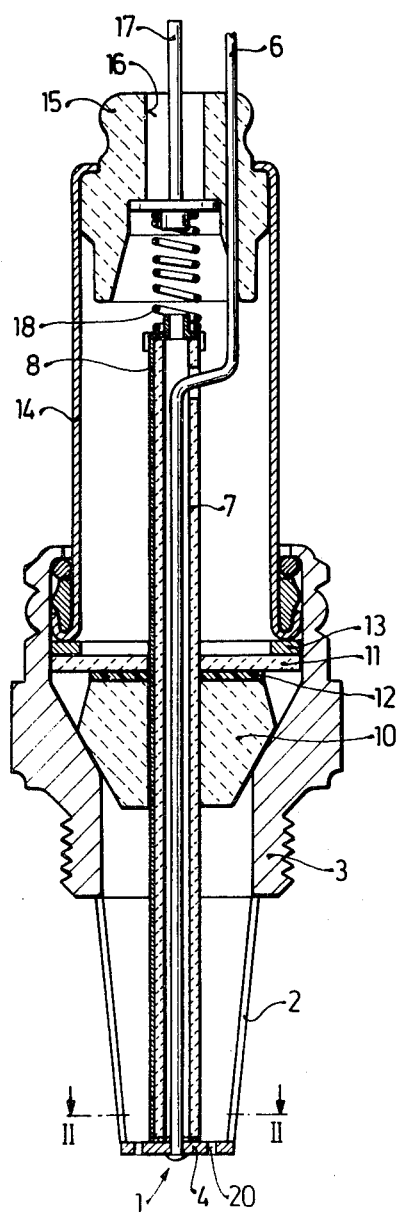
FIG. 1 is a longitudinal sectional view through the sensor.
Figure 3:
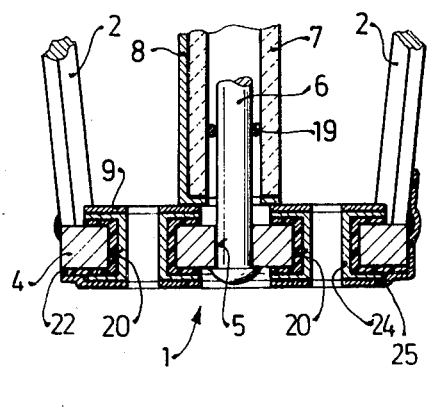
FIG. 3 is a fragmentary sectional view of the sensing end, to a greatly enlarged scale.

The sensor has a plate or disk-like measuring cell 1 which is secured by support struts 2 to a housing or socket 3. The measuring cell 1 (FIG. 3) has a circular metallic disk or plate 4 which is formed with a central opening 5 to which a supply cable 6 for heater current is connected. Preferably, the supply cable 6 is riveted into the central opening 5; beyond the rivet, the cable may be insulated. The supply cable 6 is surrounded by a ceramic tube 7 which extends through the socket 3. Cable 6 is laterally carried out of the tube 7 through an opening therein for connection to the positive terminal of a heater current source (not shown), for example the battery of an automotive vehicle. The outside of ceramic tube 7 has a conductive path 8 (FIG. 3) applied thereto. Path 8 can be made by any suitable known method, for example by vapor deposition of a metal on the ceramic tube 7. The lower end of conductive path 8 is in electrical contact connection with a catalytically inactive electrode 9 of the measuring cell system 1. The electrode 9 is classified as an "inactive" electrode although it may be slightly catalytically active; it is less catalytically active, however, than another electrode 25 applied to the other side of plate 4 to a solid electrolyte body 24, as will appear in detail below. The ceramic tube 7 (FIG. 1) is guided within the socket 3 by a guide bushing 10 to center tube 7 in the socket. A cover plate 11 and a sealing plate 12 are located in the socket to secure the side bushing 10 therein. Sealing plate 12 may, for example, be slightly elastic. Axial placement of the bushing 10, sealing plate 12 and abutment disk 11 is ensured by a snap ring 13, for example a C-ring. The guide element 10 has a conical outer surface which fits in a corresponding conical seat within the interior of the socket 3. The upper end of the housing 3 is open; it is protected by a protective sleeve 14 which is closed off at its upper end by a stopper 15. Stopper or terminal end 15, the guide element, the cover disk 11 and seal 12 are all made of insulating material. Except for the seal 12, they may be made of a plastic, mica, or asbestos or, preferably, a suitable ceramic material. The connecting line 6 is carried through the stopper 15 to the outside of the sensor. The stopper 15 is additionally formed with a central opening 16 through which a sensing connector 17 extends outwardly. Connection 17 is flared inside of the stopper 15 to form a disk or transverse portion, or is riveted to a similar element. A contacting spring bears against this disk or transverse rod-like portion which bears, at the other end, against a suitable bearing stub formed on the upper end of the ceramic tube 7. The spring surrounds a portion of the outer circumference of tube 7 to be in electrical contact engagement with the conductive path 8. Suitable centering pins or stubs can also be provided at the terminal 17 to center the spring within the sleeve 14 and to ensure reliable engagement of the spring 18 with conductor 17 and conductive path 8. Any other additional centering disks or star-shaped centering elements may be used if necessary. It has also been found desirable to center the conductor 6 within the interior of the ceramic tube 7 by one or more elastically deformable rings 19, one of which is shown in FIG. 3. These rings may be similar to O-rings. Socket 3 is formed with an outer thread to permit introduction of the entire sensor into the exhaust gas stream of a motor vehicle by screwing the sensor into a suitably tapped opening formed in the exhaust gas line from the internal combustion engine. The arrangement within the exhaust gas line is such that the lower portion of the sensor with the measuring cell 1, the attachment struts 2 and the lower portion of the housing 3 extend directly into the stream of exhaust gases.

Figure 2:
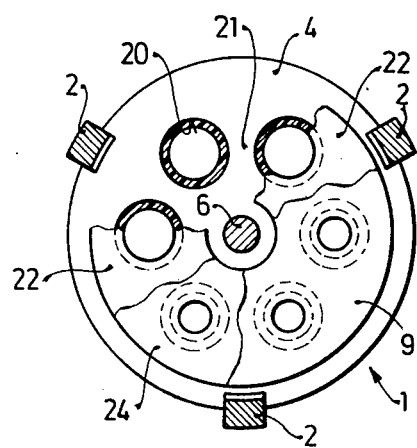
FIG. 2 is a bottom view of the inside of the sensing cell arrangement of FIG. 1, looked at from line II—II of FIG. 1, and partially in section.

Measuring cell 1 is best seen by reference to FIGS. 2 and 3. Plate 4 is formed with circular openings or cutouts 20 which are concentrically positioned on plate 4 with respect to the center thereof. This shape of plate 4 provides connecting portions 21 therein between the openings 20. The struts 2 are made of electrically conductive material and are conductively connected with the edge of the plate 4 on the one hand, and electrically conductive and mechanically connected to housing 3, on the other. Housing 3 is electrically conductively connected by means of a thread with the chassis or ground connection of the vehicle or engine. Normally, this is the negative terminal of the vehicle battery which forms the heater current source. When connection cable 6 is connected to the positive terminal of the heater current source, current will flow through cable 6, plate 4, and then to the attachment points of the struts 2 and returned to the socket 3 and then to chassis and through chassis (not shown) of the vehicle, or the ground system of the engine to the negative terminal of the battery. The current density is enhanced in the region of the connecting strips 21 between the openings 20. By suitable dimensioning of the openings leaving suitably dimensioned connecting strips 21, substantial heating results due to the decreased cross-sectional area available for current flow.

In accordance with a feature of the invention, the plate 4 is coated at both facing sides with a ring-shaped insulating layer 22 which extends through the openings 20 and also covers the interior rings or inner walls formed by the openings 20. The insulating layer 22 is covered essentially entirely by a layer of solid electrolyte material 24 which also extends through the openings 20. The solid electrolyte material 24 is covered at the upper side of the plate 4 by the catalytically inactive, or only slightly active, electrode 9. A catalytically active electrode 25 covers, or essentially covers, the solid electrolyte body 24 at the lower side of the plate 4. Catalytically active electrode 25 is carried out at least at one side over the lateral edge of plate 4 to be electrically conductively connected to at least one of the support struts 2, so that the ground or chassis connection 2 for the heater current will, simultaneously, form the ground or chassis connection 2 for the measuring cell sensing voltage. If desired, the insultation layer 22 can be carried around the outer side of the plate 4 and a separate electrode secured to lower, catalytically active electrode 25 to provide a separate sensing terminal, for subsequent connection to a conductor similar to conductor 6 for example, or separate ground connection to the socket 3.

The insulating layer 22 is preferably applied to plate 4 by means of a plasma spraying. The sold electrolyte layer 24 is preferably applied over the insulating layer 22, after it has been applied, also by plasma spraying. The outer edge of plate 4 and the center of plate 4 at both sides is masked before spraying to provide an electrical connection area for cable 6 to plate 4 and, if desired, for electrical connection of catalytically active electrode 25 to support struts 2, as shown at the right side of FIG. 3. Electrodes 9 and 25 are preferably applied to the solid electrolyte body 24 by vapor deposition. Care should be taken that the catalytically inactive electrode 9 which, for example, may be made of gold, is electrically insulated from and isolated with respect to plate 4. The catalytically active electrode 25, however, can extend over the uninsulated edge of plate 4 and up to the connecting strut 2 as shown at the right side of FIG. 3. The catalytically active electrode may consist of platinum, palladium, or a palladium silver alloy. The catalytically active electrode 25, if connected as shown, will be at reference or chassis or ground potential, the measuring signal being derived between the measuring or sensing connection 17 and ground or chassis to which socket 3 is connected.

Various changes and modifications may be made. In one suitable illustrative example, plate 4 was made of an alloy of 30% Ni, 19% Cr, 0.15% Ti, 0.15% Al and the balance Fe with a thickness of 1 mm; it was circular and had a diameter of 10 mm, formed with six openings of 1.3 mm diameter. An insulating layer 22 of $Al_2O_3$ was applied thereover, over which a solid electrolyte layer 24 of 0.2 mm thickness was applied. Connection of cable 6 to a 12 V nominal voltage battery resulted in a heater current of about 6 A which heated the solid electrolyte 24 to a temperature of about 700° C. within 17 sec.

The material of the solid electrolyte layer 24 was $ZrO_2$.

I claim:

1. Oxygen sensor to determine the oxygen content in gases having a measuring cell including a solid electrolyte body (24) comprising
   a metallic carrier plate (4) formed with openings (20) therein leaving connecting portions (21) of plate material between the openings;
   heating electrode connections (2, 6) secured to the carrier plate and positioned with respect to said openings to locate the openings between the heating electrodes to provide an electric path of reduced cross section and thus a heating resistance path through said connecting portions (21);

an insulating covering (22) over the surfaces of said plate including the edges and internal rims of said openings (20), said electrolyte body (24) being applied as a layer of electrolyte material on said insulating covering (22) on the plate (4) including the portions of insulating material extending over the edges and internal rims of the openings whereby the plate will form a support for said electrolyte and provide for heating thereof;

a catalytically active electrode (25) applied to said layer of electrolyte body (24) at one side of the plate;

a catalytically inactive electrode (9) applied to said layer of electrolyte body (22) at the other side of said plate (4);

and means (2, 3) supporting said plate, with said layer thereon, for exposure of both sides of said plate, and hence both said electrodes (9, 24) to the gases, the oxygen content of which is to be determined.

2. Sensor according to claim 1, wherein the plate (4) is an essentially circular disk;

and the openings (20) are located on a ring concentric with the center of said disk (4).

3. Sensor according to claim 1, wherein the insulating covering (22) comprises a plasma-sprayed covering secured on said plate.

4. Sensor according to claim 1, wherein said electrolyte body (24) formed as a layer on said insulating covering (22) comprises a plasma-sprayed electrolyte material secured to said insulating covering.

5. Sensor according to claim 4, wherein the insulating covering (22) comprises a plasma-sprayed covering secured on said plate.

6. Sensor according to claim 5, wherein the plate (4) is an essentially circular disk;

and the openings (20) being located on a ring concentric with the center of said disk (4).

7. Sensor according to claim 1, to determine the oxygen content of exhaust gases in an internal combustion engine wherein the support means comprises a socket (3);

electrically conductive support means (2) extending from the socket and connected to and supporting said plate at circumferential locations thereof and further forming a terminal of one of said heating electrode connections;

an insulated conductor (6) electrically connected to the center of said plate (4) and forming a terminal of another heating electrode connection;

and a tube (7) positioned centrally with respect to said plate and being at least in part electrically conductive and in electrically conductive connection with one (9) of said electrodes (9, 24) applied to the electrolyte body (24).

8. Sensor according to claim 7, wherein said catalytically active electrode (25) is in electrical connection with said support means (2).

9. Sensor according to claim 7, wherein said central tube (7) is a ceramic tube;

and a conductive path (8) being formed at the outside of said tube (7) in electrically conductive connection with the catalytically inactive electrode (9), said catalytically inactive electrode being applied to the side of said layer of solid electrolyte body facing the socket.

10. Sensor according to claim 9, wherein the catalytically active electrode (25) is applied to the layer forming said solid electrolyte body (24) remote from said socket and is in electrical circuit connection with said plate (4).

11. Sensor according to claim 10, wherein the plate (4) is an essentially circular disk;

the openings being located on a ring concentric with the center of said disk;

the insulating covering (22) comprising a plasma-sprayed covering secured on said plate (4);

and the electrolyte body (24) comprising a plasma-sprayed electrolyte material formed as a layer on said insulating covering (22).

12. Sensor according to claim 10, wherein the plate (4) is an essentially circular disk;

and the openings (20) are located on a ring concentric with the center of said disk (4).

13. Sensor according to claim 12, wherein the insulating covering (22) comprises a plasma-sprayed covering secured on said plate.

14. Sensor according to claim 13, wherein said electrolyte body (24) formed as a layer on said insulating covering (22) comprises a plasma-sprayed electrolyte material secured to said insulating covering.

* * * * *